(12) United States Patent
Chen et al.

(10) Patent No.: US 11,540,714 B2
(45) Date of Patent: Jan. 3, 2023

(54) SHEAR WAVE BASED ELASTICITY IMAGING USING THREE-DIMENSIONAL SEGMENTATION FOR OCULAR DISEASE DIAGNOSIS

(71) Applicant: The Regents of the University of California, Oakland, CA (US)

(72) Inventors: Zhongping Chen, Irvine, CA (US); Youmin He, Irvine, CA (US); Yueqiao Qu, Irvine, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 810 days.

(21) Appl. No.: 16/402,591

(22) Filed: May 3, 2019

(65) Prior Publication Data

US 2019/0335996 A1    Nov. 7, 2019

Related U.S. Application Data

(60) Provisional application No. 62/666,980, filed on May 4, 2018.

(51) Int. Cl.
*A61B 3/14*         (2006.01)
*A61B 3/12*         (2006.01)
(Continued)

(52) U.S. Cl.
CPC ............ *A61B 3/1225* (2013.01); *A61B 3/102* (2013.01); *A61B 3/14* (2013.01); *A61B 5/7264* (2013.01); *A61B 8/10* (2013.01); *A61B 8/4488* (2013.01); *A61B 8/4494* (2013.01); *A61B 8/485* (2013.01); *A61B 8/488* (2013.01); *A61B 8/5261* (2013.01);
(Continued)

(58) Field of Classification Search
CPC ......... A61B 3/102; A61B 3/1225; A61B 3/14; A61B 5/0051; A61B 5/442; A61B 5/7264; A61B 8/10; A61B 8/4416; A61B 8/4488; A61B 8/4494; A61B 8/485; A61B 8/488; A61B 8/5261; G06K 9/6224; G06T 2207/10101; G06T 2207/10132; G06T 2207/20081; G06T 2207/20116; G06T 2207/20221; G06T 2207/30041; G06T 7/0012; G06T 7/12; G06V 2201/03; G06V 40/193
See application file for complete search history.

(56) References Cited

U.S. PATENT DOCUMENTS 10,231,706 B2    3/2019   Chen et al.

*Primary Examiner* — Mark D Remaly
(74) *Attorney, Agent, or Firm* — Nguyen Tarbet LLC

(57) ABSTRACT

Retinal diseases, such as age-related macular degeneration (AMD), are the leading cause of blindness in the elderly population. Since no known cures are currently present, it is crucial to diagnose the condition in its early stages so that disease progression is monitored. Systems and methods for detecting and mapping the mechanical elasticity of retinal layers in the posterior eye are disclosed herein. A system including confocal shear wave acoustic radiation force optical coherence elastography (SW-ARF-OCE) is provided, wherein an ultrasound transducer and an optical scan head are co-aligned to facilitate in-vivo study of the retina. In addition, an automatic segmentation algorithm is used to isolate tissue layers and analyze the shear wave propagation within the retinal tissue to estimate mechanical stress on the retina and detect early stages of retinal diseases based on the estimated mechanical stress.

9 Claims, 9 Drawing Sheets
(6 of 9 Drawing Sheet(s) Filed in Color)

(51) Int. Cl.
*A61B 8/10* (2006.01)
*A61B 8/08* (2006.01)
*A61B 8/00* (2006.01)
*G06T 7/12* (2017.01)
*A61B 5/00* (2006.01)
*G06K 9/62* (2022.01)
*A61B 3/10* (2006.01)

(52) U.S. Cl.
CPC .............. *G06K 9/6224* (2013.01); *G06T 7/12* (2017.01); *G06T 2207/10101* (2013.01); *G06T 2207/10132* (2013.01); *G06T 2207/20081* (2013.01); *G06T 2207/20116* (2013.01); *G06T 2207/20221* (2013.01); *G06T 2207/30041* (2013.01)

SHEAR WAVE BASED ELASTICITY IMAGING USING THREE-DIMENSIONAL SEGMENTATION FOR OCULAR DISEASE DIAGNOSIS

CROSS-REFERENCES TO RELATED APPLICATIONS

This application is a non-provisional and claims benefit of U.S. Patent Application No. 62/666,980, filed May 4, 2018, the specification(s) of which is/are incorporated herein in their entirety by reference.

GOVERNMENT SUPPORT

This invention was made with government support under Grant Nos. EY026091, EY027666, EY028662 awarded by the National Institutes of Health. The government has certain rights in the invention.

FIELD OF THE INVENTION

The present invention relates to ophthalmic imaging, more particularly to elasticity imaging using optical coherence tomography (OCT) for ocular disease diagnosis.

BACKGROUND OF THE INVENTION

Age-related macular degeneration (AMD) is a progressive disease of the retina and is the leading cause of severe vision loss in the western population over 50 years of age. AMD most often induces drusen formation in the dry form, and neovascularization in wet AMD. Drusen often acts as an early sign of AMD whereas neovascularization occurs when excess blood vessels leak into the layers of the retina, signifying a later stage of disease. Current methods of diagnosis include fundus photography, which provides surface structural information of the retina, and fluorescein angiography, which is used to visualize blood vessels and leakages if neovascularization is suspected. For more accurate visualization of the entire depth of the retinal layers, optical coherence tomography (OCT) is used for non-invasive optical imaging. OCT angiography is also used to produce en face images of retinal blood vessels and diagnose abnormal regions. Once AMD is diagnosed, there is currently no known cure so disease management is necessary in various forms, including antiangiogenic drugs, radiation and laser treatments, and photodynamic therapy. Since it is important to slow down the progression of the disease through treatment, early diagnosis is essential. Although it is possible to see anatomical changes that occur with drusen formation and neovascularization, it is very difficult to diagnose in the early stages before structural changes are evident.

Recent studies show that the mechanical properties of the posterior eye also change with the onset of disease, such as in the case of angiogenesis or retinal degeneration. In particular, the mechanical stress on the retina gets altered during the early stages when drusen deposits begin to form and also later when blood vessels infiltrate. Since it is often difficult to visualize drusen when the deposits are on the micron level, it would be helpful to use an alternate means of diagnosis. In addition, since the layers of the posterior eye are made of a tight network of cells and tissues, the elasticity of different layers is expected to differ. Elastography methods based on magnetic resonance imaging, ultrasound, and optical coherence tomography, have been widely used in determining the elasticity of tissues. Optical coherence elastography (OCE) has the advantage in ocular imaging due to its high resolution (<10 um) and the transparency of ocular tissues, yet few investigations of the mechanical properties of the posterior eye have been reported. Ex-vivo retinal elasticity has been studied previously, where elasticity of only two different retinal layers were visualized and quantified based on shear wave OCE using an ultrasound transducer as excitation. However, the ultrasound excitation and OCT detection were on opposite sides, a configuration not feasible for in-vivo use where the posterior side is inaccessible.

Due to the difficulty in penetrating the posterior globe through the anterior eye and vitreous, combined with the need for high sensitivity and resolution, a solution that addresses the aforementioned issues is needed. The present invention proposes a confocal shear wave acoustic radiation force optical coherence elastography (SW-ARF-OCE) system that enables in-vivo imaging of the mechanical properties of the retina, e.g., retinal elasticity, where an ultrasound ring transducer and optical scan head are co-aligned. The present invention may be used for the quantification and diagnosis of ocular diseases in vivo.

SUMMARY OF THE INVENTION

It is an objective of the present invention to provide systems and detection methods for early diagnosis of retinal diseases based on mechanical properties measured across different layers of the retina using co-aligned and confocal excitation, as specified in the independent claims. Embodiments of the invention are given in the dependent claims. Embodiments of the present invention can be freely combined with each other if they are not mutually exclusive.

Since traditional diagnosis methods for retinal and other ocular diseases rely on the identification of structural and vascular abnormalities, they may be insufficient for early detection when the anatomical abnormalities are not yet evident. Recent studies suggest that retinal diseases such as AMD may also affect the tissue elasticity in the early stages. Additionally, any stiffness changes within the eye may alter the elasticity of the surrounding layers and structures due to the close-knit structure of the posterior eye. Therefore, the present invention proposes using a confocal SW-ARF-OCE (shear wave acoustic radiation force optical coherence elastography) system with a three-dimensional (3-D) automatic segmentation algorithm to image the elastogram of the eye noninvasively for early detection of retinal diseases. The confocal SW-ARF-OCE system allows for easy access to the posterior eye and high axial displacement sensitivity. In addition, the 3-D segmentation method isolates the tissue part and traces the shear wave propagation, allowing for retinal layer segmentation and spatial shear velocity calculation. This technique has been developed and validated with both an ex-vivo porcine tissue model and an in-vivo rabbit model, which both show the quantified elasticity variations between different posterior ocular structures. The rabbit model was measured, and the elasticity of the different retinal layers were identified in increasing stiffness from the ganglion side to the photoreceptor portions. To the best of the inventor's knowledge, the present invention demonstrates the first in-vivo elasticity mapping of the retina.

In some aspects, the present invention features an integrated SW-ARF-OCE system for in vivo imaging to characterize the biomechanical properties of ocular tissues. The present invention uniquely includes a confocal SW-ARF-OCE system with co-aligned ARF excitation and OCT detection to measure the mechanical properties of ocular tissues. Herein, an ultrasound transducer is used for acoustic excitation on the same side of OCT beam. In particular, a ring ultrasound transducer or an array ultrasound transducer of the present invention enables co-alignment of OCT and ultrasound beam. The co-alignment of ARF excitation with OCT detection increases sensitivity of the system and enables low power of ARF to be safely used for OCE imaging.

According to some embodiments, the present invention features a non-invasive system and method for detection of elasticity of retinal layers in a posterior of the eye. The system may include a confocal shear wave acoustic radiation force optical coherence elastography (SW-ARF-OCE) system, a processor operatively coupled to the SW-ARF-OCE system, and a memory operatively coupled to the processor. In some embodiments, the SW-ARF-OCE system may comprise an ultrasound transducer and an optical coherence tomography (OCT) system confocal and co-aligned with the ultrasound transducer. The OCT system and the ultrasound transducer are configured to be disposed exterior to and on a same side of the eye. The memory stores computer-readable instructions that, when executed by the processor, causes the processor to perform operations.

In some embodiments, these operations include pulsing the ultrasound transducer to generate a shear wave displacement at a first location of the retinal layers and receiving OCT signals from multiple locations along the retinal layers. The multiple locations may be lateral to the first location and the OCT signals provide a measure of a propagation of the shear wave displacement along the multiple locations of the retinal layers. The operations also includes performing a 3-D segmentation analysis on the OCT signals detected to segment the retinal layers and isolate different retinal layers for layer specified shear wave elastic analysis, tracing shear wave propagation with 3-D segmentation, calculating a shear wave propagation speed at each segmented retinal layer and generate a shear velocity map at each segmented retinal layer. A shear modulus of each segmented retinal layer may be determined based on the shear velocity map and an elastic modulus of each segmented retinal layer may be determined based on the shear modulus. The operations further include generating an elastogram of the elastic modulus of each segmented retinal layer, thereby spatially mapping elasticity of different posterior ocular layers of the retina.

In one embodiment, the SW-ARF-OCE system may further comprise a radiofrequency amplifier operatively coupled to the ultrasonic transducer, a function generator operatively coupled to the radiofrequency amplifier, and a processor operatively coupled to the function generator. The processor can pulse the ultrasound transducer by producing a baseband signal that is converted by the function generator into a sinusoidal modulated pulse signal. The sinusoidal modulated pulse signal can be amplified by the radiofrequency amplifier and fed to the ultrasonic transducer. In a preferred embodiment, the ultrasonic transducer operates in a shear wave mode and generates an acoustic beam. This acoustic beam is then applied to the first location of the retinal layers to generate the shear wave displacement in the retinal layers.

In other embodiments, the OCT system may comprise a light source, an optical isolator, an optical coupler, a reference mirror, a pair of galvo mirrors, and a camera operatively coupled to the processor. The light source can emit a light that is filtered through the optical isolator and then split by the optical coupler into a first split light that is directed to the reference mirror and a second split light that is transmitted to the pair of galvo mirrors. A position of the galvo mirrors is adjusted such that the second split light beam is confocal with the acoustic beam in a starting location, and focal on a plurality of locations on the sample, thereby enabling detection of the shear wave displacement at the plurality of locations on the sample. The detection of the shear wave displacement is in a form of scattered light, which is coupled with the reflected first split light to form an interference light. The interference light is separated by wavelength with a diffraction grating and focused onto the line scan camera. A camera signal from the camera is further processed by the processor using 3-D segmentation analysis to generate the elastogram.

In some other embodiments, the system of the present invention further includes 3-D translational stage to perform mechanical scan for additional field of view, as well as the reconstruction algorithm to form a volumetric visualization of the scanning area. In other embodiments, the system may comprise a handheld SW-ARF-OCE probe with co-aligned ARF excitation and OCT detection for clinical application.

In one embodiment, the system may comprise the in-vivo SW-ARF-OCE setup with steridrape using confocal excitation and detection. In another embodiment, the present invention may further integrate a spectrally encoded interferometric system to obtain real time enface intensity and displacement image for image registration and bulk motion removal. In yet another embodiment, the present invention may further comprise a phase resolved Doppler OCT where Doppler variance imaging methods can be used to track the ARF-induced shear wave and form a co-registered angiogram.

In some embodiments, the 3-D segmentation algorithm and shear wave analysis/quantification algorithm is used to spatially map the elasticity of different posterior ocular layers. The 3-D segmentation method may further segment the boundary of tissue part to isolate tissue Doppler OCT data. The 3-D segmentation method may further segment distinctive retinal layers, allows for layer specified shear wave elastic analysis. The 3-D segmentation method may further be performed on spatial temporal Doppler OCT data within the isolated tissue part to obtain the spatial shear wave speed. The 3-D segmentation method may further trace the shear wave propagation by obtaining the time when the shear wave arrives at each pixel within the field of view.

In some embodiments, the 3-D segmentation method includes, but is not limited to, a combination of 3-D dynamic programming and random walker algorithm. The dynamic programming is able to firstly segment a smooth boundary where pixels have relative greater gradient than their surroundings. Then the random walker algorithm is able to refine the boundaries by using the intensity information of pixels. This combination allows for robust segmentation against low signal to noise ratio and speckle noise. In other embodiments, the 3-D segmentation method may further use a combination of two other segmentation algorithms such as, for example, using gradient based algorithm to segment the boundaries first and refine it with intensity based algorithm. Other algorithms may include, but is not limited to, the methods based on graph theory, machine learning and clustering. In some other embodiments, the 3-D segmentation method may further replace the 2-D random walker algorithm with its 3-D version to achieve better smoothness. The shear wave quantification algorithm calculates the spatial wave speed by estimating the slope of wave travel distance as a function of wave arrival time at each pixel.

In one embodiment, the estimation method for the slope may comprise linear least square. Other estimation methods using any kind of least square estimation may be used for same purpose without deviating from the scope of the invention. In another embodiment, the shear wave quantification algorithm may further estimate the shear modulus using the shear wave speed and tissue density, and generate elasticity based on the relationship between Young's modulus and shear modulus.

One of the unique and inventive technical features of the present invention is the confocal and co-aligned SW-ARF-OCE system that can be disposed on an exterior side of the eye. Without wishing to limit the invention to any theory or mechanism, it is believed that the technical feature of the present invention advantageously provides for confocal and co-alignment of the ultrasound beam and OCT detection to measure the mechanical properties of ocular tissues non-invasively, and further includes automatic segmentation of the different retinal layers for measuring the elasticity across the different retinal layers. The SW-ARF-OCE system can detect quantitative elasticity using a shear wave based method with a single shot excitation that reduces the mechanical power exerted on the patient. The present invention allows for non-invasive, in-vivo imaging of the retinal layers in a posterior of eye to detect early stages of retinal diseases based on changes in elasticity of the different retinal layers. None of the presently known prior references or work has the unique inventive technical feature of the present invention.

Currently available systems include ARF excitation and OCT detection in the opposite sides of the tissue to be imaged. Such transmission mode systems cannot be used for in-vivo retina imaging because the back of the eye is inaccessible. It also suffers from a number of issues. As an example, the transmission mode systems require a directional filter to analyze the shear wave propagation in the direction of interest. As another example, cross-correlations of Doppler OCT (DOCT) data on adjacent pixels are typically performed along the temporal dimension to obtain the shear wave speed and imaging noise may easily deteriorate the measurement by affecting the pixel value. In yet another example, the measurements on the boundary between the tissue and background are unreliable because the wave speed in the background is undetectable in such systems. In addition, rapidly changing displacements may additionally degrade the OCT image quality through fringe washout in such systems.

Without wishing to limit the invention to any theory or mechanism, the present invention can overcome the aforementioned issues. Herein, the present invention discloses a reflection mode system which ensures easy access to the posterior eye ex-vivo and in-vivo. Additionally, it does not require a filter to isolate the signal. Furthermore, the 3-D segmentation algorithm of the present invention allows for isolation of tissue data from background signal, as well as the isolation between different anatomical structures. For shear wave speed calculation, it is also robust against noises because the algorithm traces shear wave using the entire data set instead of simply calculating between adjacent pixels. The combination of the random walker and dynamic programming algorithms of the present invention ensures robustness for segmenting images with shear wave induced displacement.

One of the challenges in analyzing retinal OCE data is segmentation. It is necessary to segment the boundaries across layers so that data from each individual layer can be isolated for layer specific elasticity analysis. Another challenge of shear wave elasticity analysis is to trace the location of the wave surface over time for the purpose of wave speed calculation. With layered Doppler OCT data and the segmentation algorithm, the wave surface as a function of time in each layer can be segmented to calculate the shear wave velocity at every location.

Any feature or combination of features described herein are included within the scope of the present invention provided that the features included in any such combination are not mutually inconsistent as will be apparent from the context, this specification, and the knowledge of one of ordinary skill in the art. Additional advantages and aspects of the present invention are apparent in the following detailed description and claims.

BRIEF DESCRIPTION OF THE DRAWINGS

This patent application contains at least one drawing executed in color. Copies of this patent or patent application publication with color drawing(s) will be provided by the Office upon request and payment of the necessary fee.

The features and advantages of the present invention will become apparent from a consideration of the following detailed description presented in connection with the accompanying drawings in which:

FIG. 10A is an OCT of porcine central retina. FIG. 10B is a velocity map of the shear wave propagation. FIG. 10C is an elastogram of the corresponding region. FIG. 10D is an H&E staining of the porcine retinal layers, where: i. optic nerve fibers (ONF) & ganglion cell layer (GCL); inner plexiform layer (IPL); iii. inner nuclear layer (INL) & outer plexiform layer (OPL); iv. outer nuclear layer (ONL); and v. photoreceptors (PR).

FIG. 11A is an OCT of rabbit central retina. FIG. 11B is a shear wave velocity map. FIG. 11C is an elastogram of corresponding region. FIG. 11D is an H&E histology showing some retinal detachment, where: i. nerve fiber, ganglion cell, & inner plexiform; ii. inner nuclear, outer plexiform, & outer nuclear; iii. RPE; iv. choroid; and v. sclera.

DESCRIPTION OF PREFERRED EMBODIMENTS

Following is a list of elements corresponding to a particular element referred to herein:

| | |
|---|---|
| 102 | light source |
| 104 | isolator |
| 106 | optical coupler |
| 108 | reference mirror |
| 110 | radiofrequency amplifier |
| 112 | ultrasound transducer |
| 114 | galvo mirrors |
| 116 | function generator |
| 118 | sample |
| 120 | CMOS camera |
| 122 | processor |
| 202 | sample |
| 204 | acoustic radiation force (ARF) beam |
| 206 | optical coherence tomography (OCT) beam |
| 402 | galvo position |
| 404 | camera trigger |
| 406 | ultrasound modulation |
| 408 | displacement image |
| 410 | shear modulus map |

Retinal diseases, such as age-related macular degeneration (AMD), are the leading cause of blindness in the elderly population. Since no known cures are currently present, it is crucial to diagnose the condition in its early stages so that disease progression is monitored. Recent advances show that the mechanical elasticity of the posterior eye changes with the onset of AMD. The present invention provides systems and methods for quantitative mapping of the mechanical elasticity of the posterior eye in vivo using confocal shear wave acoustic radiation force optical coherence elastography (SW-ARF-OCE) described with reference to FIG. 1. More specifically, the confocal and co-aligned geometry of the ultrasound and the optical probing via OCT allows for in vivo imaging of the retina and thus determine the mechanical properties of each layer of the retina, as discussed below.

According to some embodiments, the present invention features a confocal shear wave acoustic radiation force optical coherence elastography (SW-ARF-OCE) system. The SW-ARF-OCE system includes an ultrasound transducer and an optical scan head that are confocal and co-aligned to facilitate in-vivo study of the retinal elasticity. In addition, an automatic segmentation algorithm is used to isolate retinal layers and analyze the shear wave propagation within the retinal tissue.

The present SW-ARF-OCE system has an ultrasonic transducer and an optical coherence tomography system on the same side, which makes for in vivo use feasible where the posterior eye is inaccessible. The 3-D segmentation analysis comprising 3-D dynamic programming and random walker algorithm allows for robust segmentation against low signal to noise ratio and speckle noise. It enables the present system to use low power shear wave mode safe for medical standards. Prior systems teach away from using shear wave mode because these systems could not get enough sensitivity from shear wave mode without increasing the power to medically harmful levels. Further still, these prior systems commonly use a directional filter to analyze the shear wave propagation whereas in the present invention, a filter is not required to isolate the signal.

Figure 1:
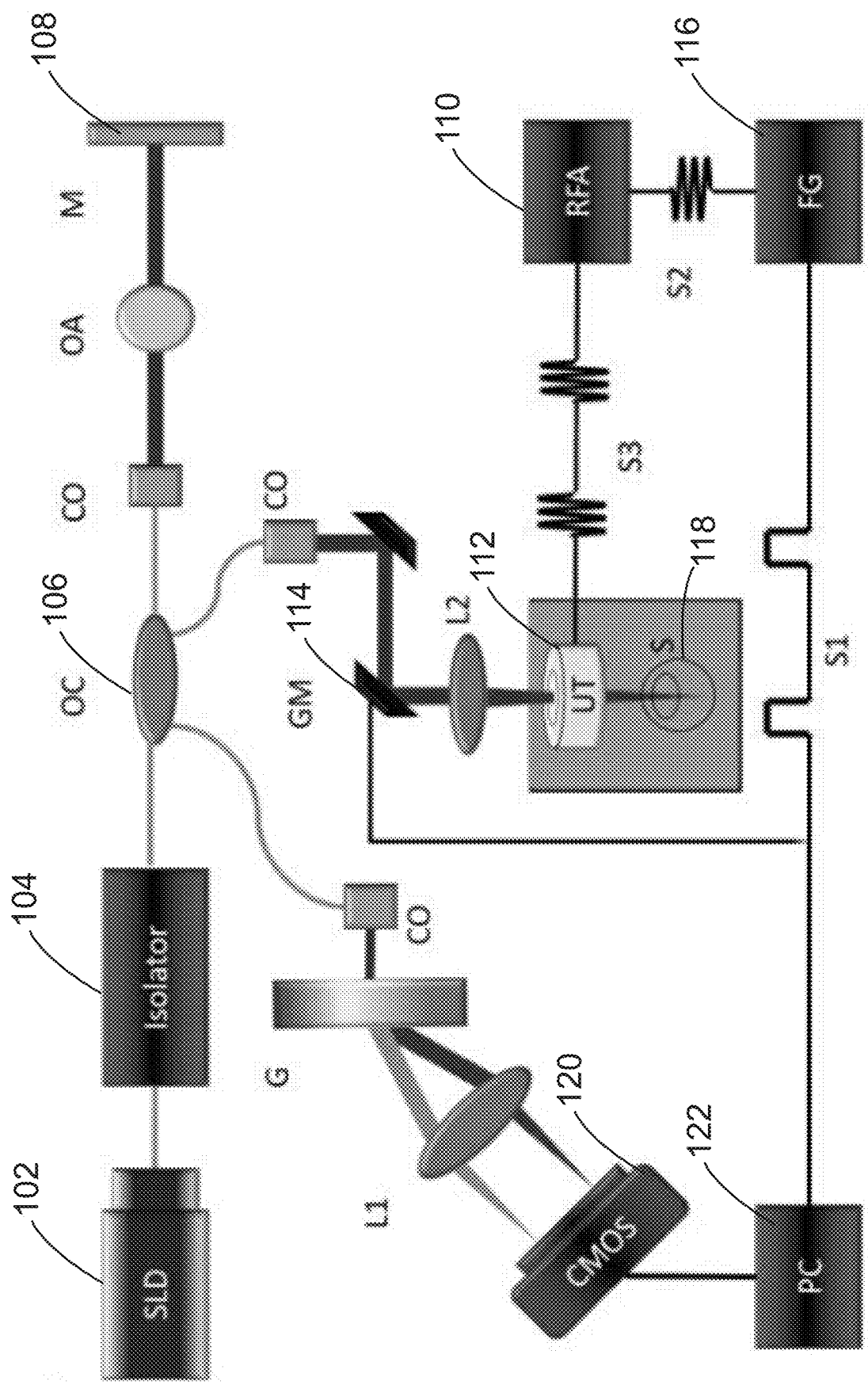
FIG. 1 shows a schematic diagram of a shear wave acoustic radiation force optical coherence tomography (SW-ARF-OCE) system according to an embodiment of the present invention, where SLD: superluminescent diode, OC: optical coupler, CO: collimator, OA: optical attenuator, M: mirror, GM: galvanometer mirrors, L1/L2: lens, UT: ultrasound transducer, S: sample, RFA: radiofrequency amplifier, FG: function generator, G: grating, S1: baseband signal, S2: modulated signal, and S3: amplified modulated signal.

Referring to FIG. 1, a schematic diagram of a shear wave acoustic radiation force optical coherence tomography (SW-ARF-OCE) system is shown. Light emitted from a light source (102) is filtered through an optical isolator (104) and split with an optical coupler (106). As a non-limiting example, the light source (102) may be a superluminescent diode. Light may be split towards a reference arm (containing a reference mirror (108)) and additionally towards a sample arm (containing a sample (118)). In some embodiments, 20% of the light may be transmitted to the sample (118) in the sample arm, and 80% of the light may be redirected to the reference mirror (108) in the reference arm. In other embodiments, 30% of the light may be transmitted towards the sample, and 70% of the light may be transmitted towards the mirror M. Other proportions may be used without deviating from the scope of the invention. As such, for in-vivo imaging of biological samples such as the retina, for example, the amount of light transmitted towards the sample may be selected so that the light reaching the sample is within the ANSI safety limits.

Glass imaging windows may be placed in the reference arm for dispersion compensation. In the sample arm, galvo mirrors (114) may be used for B-M mode scanning, and a scan lens (124) may be used to penetrate through an ultrasound transducer (112) and into the sample (118). In a non-limiting example, the scan lens (124) may include a focal length of about 54 mm. In some embodiments, the ultrasound transducer may be ring transducer or array transducer that allows confocal and co-alignment of the ultrasound beam and OCT detection. The sample may include a posterior eye globe, for example. Scattered signal from the sample arm may be coupled together with the reflected reference arm signal and sent to a detector arm comprising a detector. At the detector, an interference signal of the scattered signal and the reference signal is generated. The interference signal is separated by wavelength with a diffraction grating and focused onto a line scan CMOS camera (120). The signal is processed and transformed into depth-resolved intensity and phase information.

In some embodiments, the ultrasound beam may be delivered via the ring-shaped transducer or array transducer and the returned optical signal may be detected on the same side of the sample using the optical coherence tomography detector of the system shown in FIG. 1. The ring-shaped transducer or array transducer design is a non-limiting example of the ultrasound transducer design that allows for the confocal launching of the ultrasound and the optical beams. For instance, the ultrasound transducer can be a ring shaped transducer that allows for the optical beams to pass through the central aperture of the ring, as depicted in FIG. 1. Herein, the excitation and the detection occur in parallel on the same side. Prior systems apply ultrasound excitation on the retina from the back of the eye, which is not possible for in-vivo applications. By having both the excitation and the detection on the same side, the present invention can be integrated with ophthalmic imaging system thus, enabling in vivo differentiation of retinal tissues for angiogenesis or retinal degeneration diagnosis and treatment. Other designs of the transducer that allow for such confocal launching of the beams may be used without deviating from the scope of the invention.

As a non-limiting example, the system may include a 50 kHz spectral domain optical coherence tomography (SD-OCT) system with a central wavelength of 890 nm and bandwidth of 144 nm may be used for the detection of tissue structure and response to stimulation. In a non-limiting example, the ultrasound transducer used for pulsed tissue excitation may include a ring ultrasound transducer or an array ultrasound transducer. Herein, the ultrasound transducer is used to generate a shear wave displacement in the sample. Any other way of imparting the shear wave displacement in the sample may be used without deviating from the scope of the invention.

The excitation duration was limited to 1-2 ms while the optical detection speed was 50 kHz. For the shear wave excitation, a baseband signal (S1) is given by a processor (122) to a function generator (116), which converts it into a sinusoidal modulated pulse signal with 1-2 msec duration. This pulse is amplified by a radiofrequency amplifier (110) by approximately 42 dB and fed to the ultrasound transducer (112). A pressure is applied onto the sample, initiating the propagation of the shear wave from the focal region to the peripheral areas. The detection scanning scheme is shown in FIG. 2, where an ultrasound excitation beam (204) is given at location P0 of sample (202), and B-M mode detection occurs along the lateral direction from P1 to Pn. Herein, the ultrasound excitation beam may be referred to as the acoustic radiation force (ARF) beam and the B-M mode detection may be referred to as the OCT beams.

Figure 3:
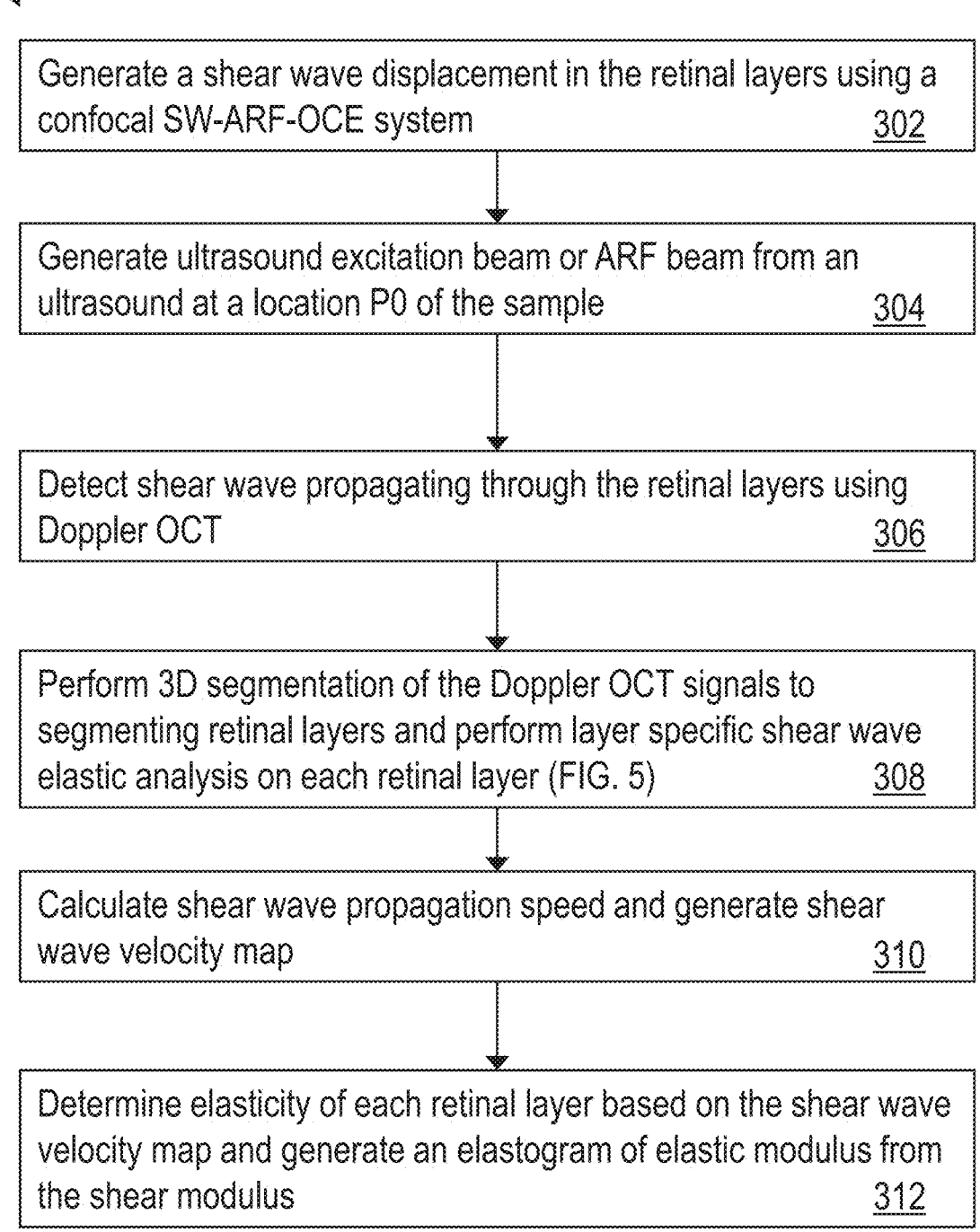
FIG. 3 shows a high-level flow chart depicting an example elastography method for in-vivo detection of elasticity of retinal layers in a posterior eye.

FIG. 3 shows an example elastography method (300) for in-vivo detection of elasticity of retinal layers in a posterior eye. At 302, method 300 includes generating a shear wave displacement in the retinal layers using a confocal SW-ARF-OCE system, such as the SW-ARF-OCE system of FIG. 1. At 304, an ultrasound transducer of SW-ARF-OCE system may generate the shear wave displacement at a location P0 of the sample or retina. As a non-limiting embodiment, a ring-shaped ultrasound transducer or an array ultrasound transducer may be used to generate the shear wave displacement at the location P0 of the retina.

At 306, method 300 includes detecting the propagation of the shear wave through the different retinal layers using OCT. As such, the retina comprises of many layers namely photoreceptor layer (PR), outer nuclear layer (ONL), outer plexiform layer (OPL), inner nuclear layer (INL), inner plexiform layer (IPL), and ganglion cell layer (GCL), and the shear wave displacement generated at location P0 may spread across the different layers.

Figure 4:
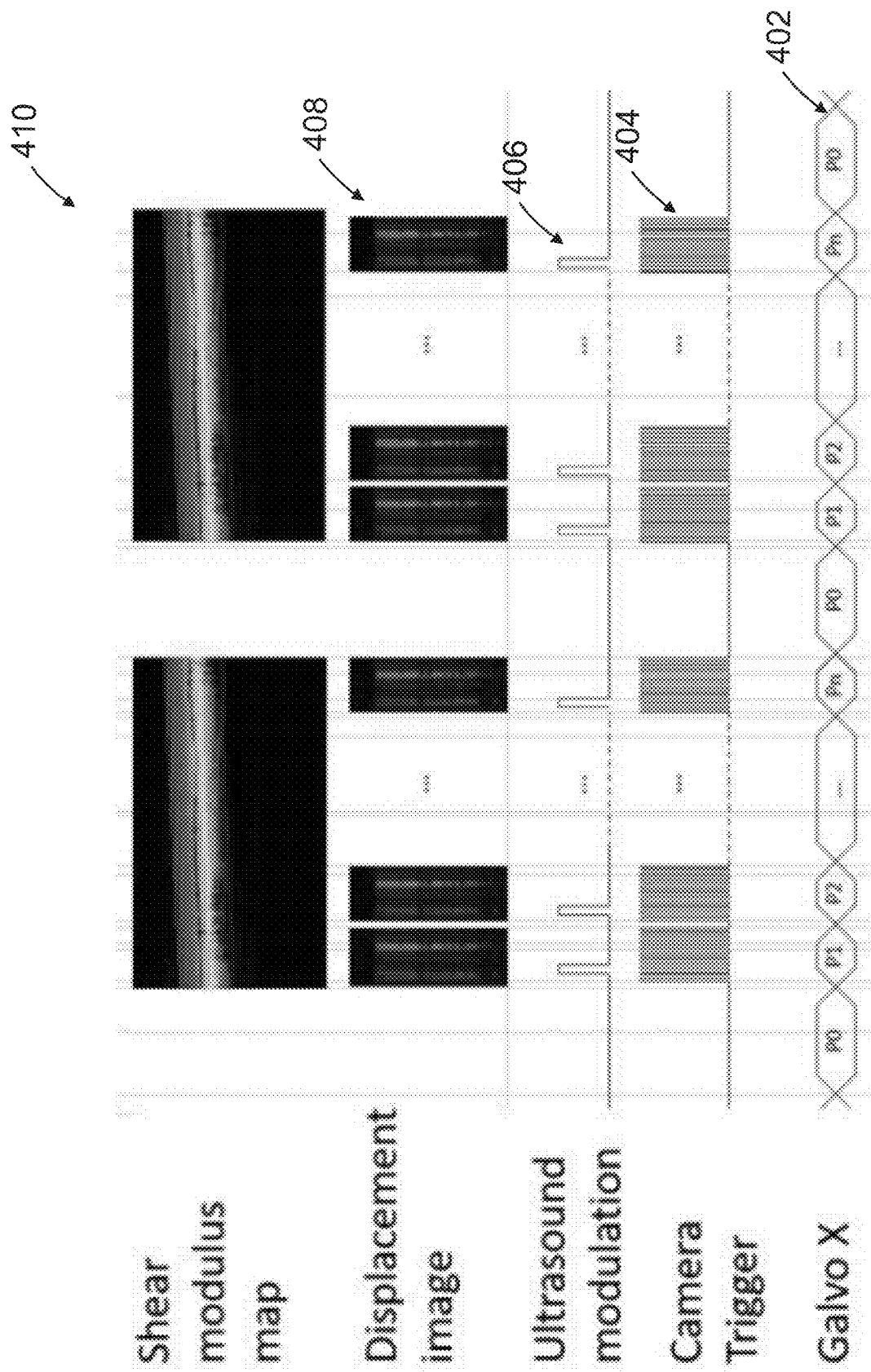
FIG. 4 shows a timing diagram of the SW-ARF-OCE system.

In order to achieve efficient and effective imaging, the entire excitation and detection process may be confocal and additionally synchronized as shown in FIG. 4. Turning now to FIG. 4, the ultrasound modulation signal (406) is delivered at the location P0 by adjusting galvo mirror position (402), for example. The OCT beam is detected at locations P1 through Pn to estimate the propagation of the shear wave through the retinal layers. Herein, the camera may be triggered to detect the OCT beam at locations P1 through Pn. As such, detecting the OCT beam includes measuring the time-delay of the light reflected from each optical interface (A-scan). A series of A-scans across the locations P1 through Pn may be used to reconstruct a cross-sectional image (known as B-scan) and a displacement image (known as M-scan), as discussed below.

In one embodiment, to obtain a B-scan showing the full lateral scanning area, an ultrasound modulation pulse is given for every 400 A-lines while the camera DAQ trigger is given for each A-line to capture the intensity and phase information at each location for 8.8 ms total, in increments of 22 us. The number of A-lines is chosen such that the entire duration and progression of the shear wave can be captured. This synchronization generates 400 B-Scan images with lateral dimension of 600 um in a total of approximately 3.5 s. After detection is completed, the galvanometer moves to the next location in increments of 1.5 um to the next location, which is well within the lateral resolution of the optical system. The M-mode displacement image is obtained at every B-scan location, and the phase-resolved displacement is post-processed to obtain the shear modulus map. Shear wave B-scan images (410) are generated by reslicing the M-scan images (408), and therefore all the B-Scan images are generated at the same time after the imaging is completed.

Figure 9:
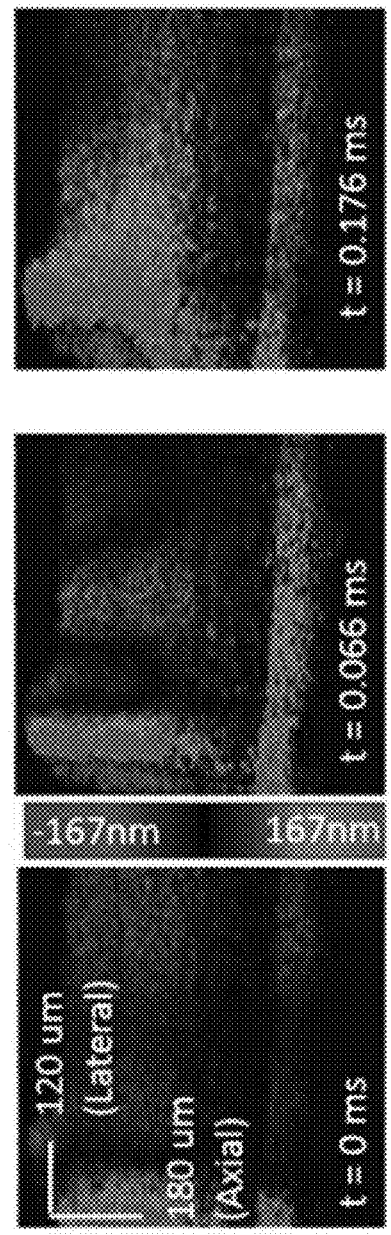
FIG. 9 shows cross-sectional data showing the wave propagation of retinal layers for an ex-vivo pig retina.

Within the 400 A-lines in M-mode at each location, the entire shear wave propagation through that point can be captured. A sample raw data for porcine retina is shown in FIG. 9, where it is apparent that different locations on the retina correspond to different propagation speeds. The transducer focal area is on the left side of the images of FIG. 9, and propagation is to the right. For example, the bottom most layer of the retina propagates the fastest and corresponds to a stiffer tissue component.

Returning to FIG. 3, method 300 detects the shear wave propagation though the retinal layers as discussed earlier. As such, one of the main challenges with retinal OCE imaging is the segmentation of the different retinal layers. Hence, at 308, method 300 includes segmenting the retinal layers using 3-D segmentation to identify each layer (PR, ONL, OPL, etc) of the retina, as shown in FIG. 5.

Figure 5:
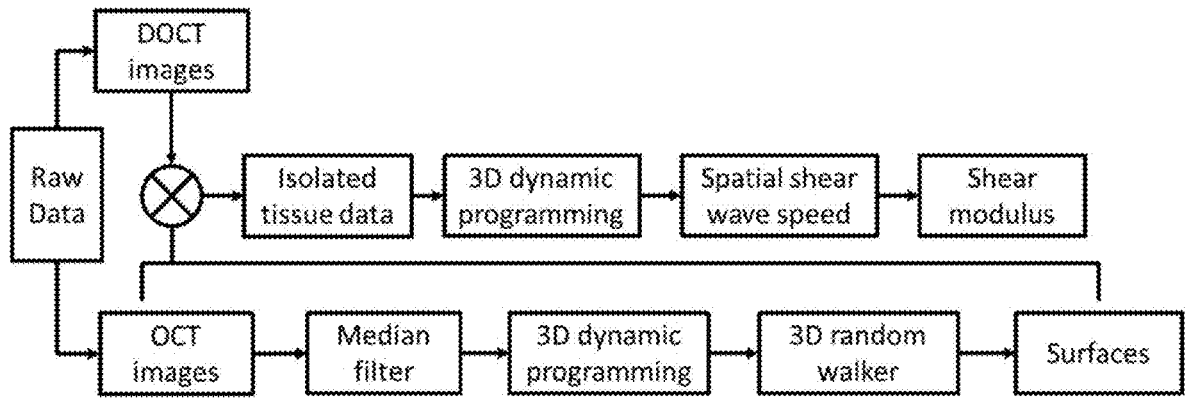
FIG. 5 shows a flow diagram demonstrating post-processing steps performed on raw data to generate shear modulus of retinal layers.

Turning now to FIG. 5, a schematic diagram that outlines the core steps of the 3-D segmentation method for mapping the shear modulus is shown. Herein, the OCT intensity image is used to visualize the retinal layered structure. Before segmentation, a 3-D median filter is applied to the volumetric data for noise reduction. By performing dynamic programming on the entire data set, the photoreceptor layer (PR) is firstly segmented. Then the segmentation is limited to the region above the surface of the PR, and the surface of the nerve fiber layer (NFL), which is on top of the retina, can be obtained. The other layers can also be obtained by limiting the region of segmentation based on the segmented layers.

Thus, the dynamic programming is able to firstly segment a smooth boundary where pixels have relative greater gradient than their surroundings. Then, the random walker algorithm is able to refine the boundaries by using the intensity information of pixels. This combination allows for robust segmentation against low signal to noise ratio and speckle noise. In some embodiments, the 2-D random walker algorithm may be replaced with a 3-D version to achieve better smoothness.

In other embodiments, the 3-D segmentation method may further use a combination of two other segmentation algorithms. For example, a gradient based algorithm may be used to segment the boundaries first and then refine them with intensity based algorithm. Other algorithms may include, but are not limited to, methods based on graph theory, machine learning and clustering. In some embodiments, the 3-D segmentation method may further replace the 2-D random walker algorithm with its 3-D version to achieve better smoothness.

In further embodiments, the segmented surfaces may then be used to isolate the tissue data from Doppler OCT images so that the background signal may not affect the calculation of the shear modulus. Herein, Doppler OCT images are used to visualized the shear wave induced axial displacement along its propagation direction. By performing the 3-D dynamic programming segmentation on the isolated tissue data in the depth direction, the depth resolved arrival time of the shear wave to each scanning location can be obtained. More specifically, the particle displacement changes rapidly upon arrival of the shear wave, resulting in gradient peaks that are traceable by the 3-D dynamic programming algorithm. The propagation speed is calculated for each location based on the slope of the segmented wave trace. The velocity is based on the change in location over the time period, from which the shear wave velocity map is obtained.

Returning to FIG. 3, once the 3-D segmentation is performed using the Doppler OCT signals at 308, method 300 proceeds to 310, where a shear wave propagation speed is calculated and a shear wave velocity map is generated. As such, the shear wave propagation speed may be determined by estimating a slope of wave travel distance as a function of wave arrival time at each pixel.

Herein, the segmented layers are applied to the displacement map, where the shear wave propagation surfaces for each layer is segmented as well. Next, the propagation speed is calculated for each location based on the slope of the segmented wave propagation for each layer. The estimation method for the slope may include, but is not limited to, linear least square. Other estimation methods using any kind of least square estimation may be used for the same purpose. The shear wave quantification algorithm may further estimate the shear modulus using the shear wave speed and tissue density, and generate elasticity based on the relationship between Young's modulus and shear modulus.

The velocity is based on the change in location over the time period, and the shear wave velocity map can be obtained at 310. The relationship between the velocity ($C_s$) and the shear modulus ($\mu$) can be described with the equation: $\mu = \rho C_s^2$, where $\rho$ is the tissue density of approximately 1 kg/m$^3$. The elastic modulus is approximately 3 times the shear modulus and can be calculated and mapped out as an elastogram, at 312. In some embodiments, co-registered images may be generated based on one or more OCT signals and the elastogram. As an example, an OCT image, a Doppler OCT image, an OCT angiogram, and an OCE image may be generated based on the signals detected and generated based on the analysis performed on the detected signals. In addition, the co-registered OCT image, Doppler OCT image, OCT angiogram and OCE image may be displayed simultaneously. In this way, the confocal SW-ARF-OCE imaging methods described herein may be used to detect retinal diseases, such as for example AMD, based on tissue elasticity in early stages measured across the different layers of the retina.

Although the systems and methods described herein have been applied for the detection of elasticity in the retina, it is to be understood that the present invention is not limited to said application. In some embodiments, the systems and methods of the present invention may be adapted for elasticity imaging of an entire eye globe. For example, the systems and methods may be used in elasticity imaging of the cornea, iris, lens, vitreous, optic nerve head, and other parts of the eye globe.

EXAMPLE

The following is a non-limiting example of the present invention. It is to be understood that said example is not intended to limit the present invention in any way. Equivalents or substitutes are within the scope of the present invention.

System Setup

Figure 2A:
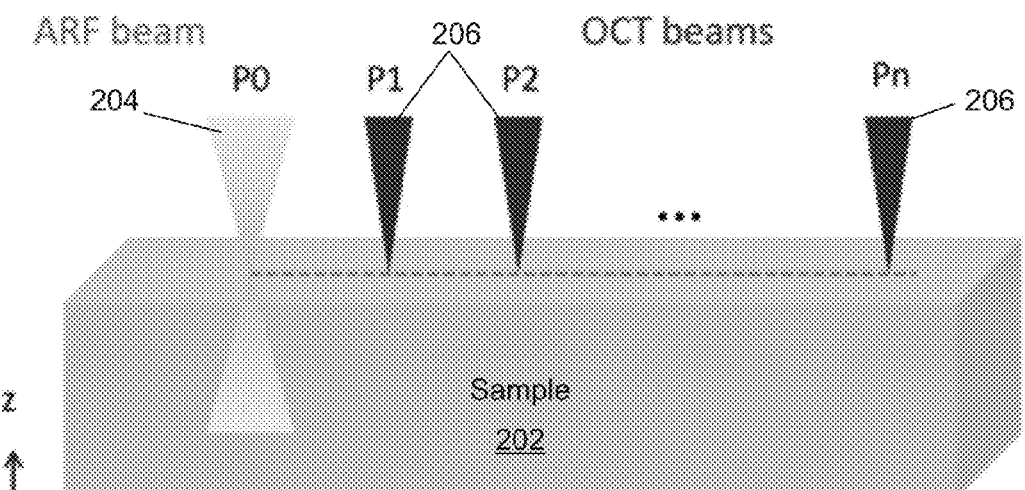
FIG. 2A shows a schematic diagram of a scanning scheme, according to an embodiment of the present invention.

In some embodiments, a customized 50 kHz spectral domain optical coherence tomography (SD-OCT) system with a central wavelength of 890 nm and bandwidth of 144 nm is used for the detection of tissue structure and response to stimulation. The imaging depth range is 2.9 mm while the penetration depth in tissue is approximately 1.5 mm. In some other embodiments, a 4.5 MHz ring ultrasound transducer was used for pulsed tissue excitation. The excitation duration was limited to 1-2 ms while the optical detection speed was 50 kHz. The optical setup and the ex-vivo sample setup are shown in FIG. 2A, where a phosphate buffered saline (PBS) is used as the medium for ultrasound propagation as well as preservation of ocular tissue.

Ex-Vivo Porcine Study

For ex-vivo porcine eye preparation, the porcine eyeball was obtained within 24 hours of death. Since the eyeball was no longer fully transparent due to degradation, the anterior portion of the eye, including the cornea and the lens was removed along the iris. The vitreous was still attached to the retina and was kept in place during imaging to avoid retinal detachment. A 0.8% agar phantom was moulded around the posterior globe and used to keep the eye in place during imaging as well as to help preserve the shape of the posterior globe and prevent detachment. The sample was kept in phosphate-buffered saline during imaging to preserve freshness and as a medium for ultrasound propagation.

Figure 10A:
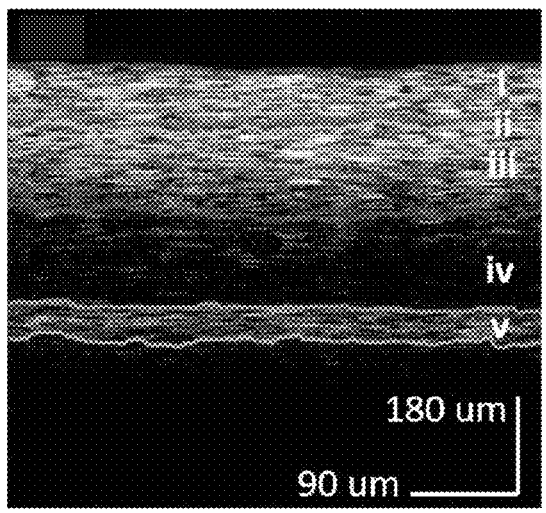
FIGS. 10A-10D show ex-vivo porcine retina results.
Figure 10B:
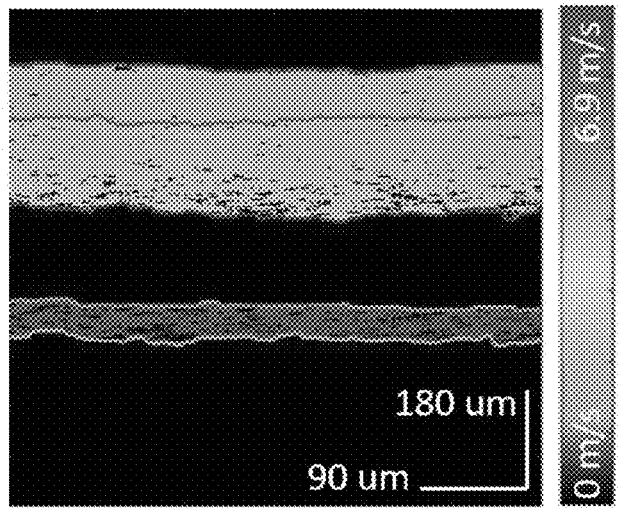
Figure 10C:
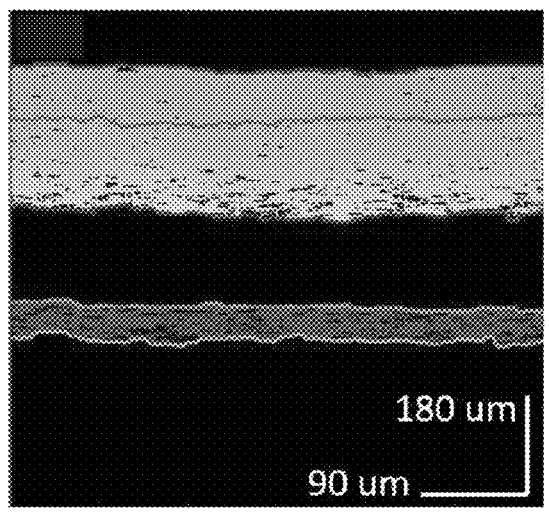
Figure 10D:
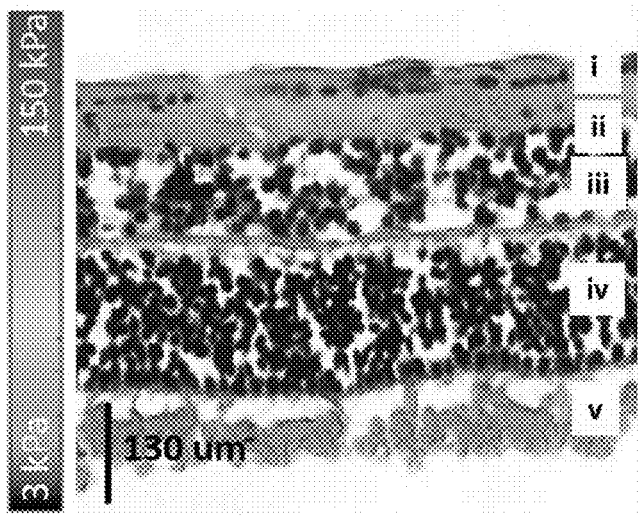

In order to test the confocal excitation and detection setup, imaging was first performed on an ex-vivo porcine retina using the same OCT system. The central retina region approximately 2 mm from the optic nerve on the temporal side was identified and imaged. The shear wave travels for over 700 um in the ex-vivo porcine retinal tissue and the system is capable of visualizing wave propagation in the whole depth of view. The OCT intensity map is shown in FIG. 10A where segmentation was performed and five different layers were isolated. Next, the corresponding shear wave velocity map and elastogram were calculated according to the above algorithm and shown in FIGS. 10B and 10C, respectively. Finally, a Haemotoxylin and Eosin (H&E) histology slide of a porcine retina is shown in FIG. 10D, where the five layers could be matched. Layer iv. was omitted during the analysis due to low OCT scattering signal in the outer nuclear layer. Retinal detachment was observed and most likely due to detachment during the removal of the anterior portion and also due to the histology process.

The elasticity results of the porcine retina are summarized in Table 1 below, where the mean and standard deviations for each layer are listed and plotted. The elasticity increased from approximately 6 kPa on the ganglion side to over 140 kPa on the photoreceptor side. Since the photoreceptor side is close to the sclera of the eye globe, it is expected to be stiffer. The close-knit structure of the retinal layers interferes with the mechanical elasticity for each and is demonstrated by the gradual gradient increase in the elasticity over the layers from the ganglion side to the photoreceptors.

Table 1 is a summary of ex-vivo elasticity maps of each porcine retinal layer. ONL was omitted due to low OCT signal in the outer nuclear layer. Std (standard deviation).

| Layer | Mean | Std |
| --- | --- | --- |
| ONF&GCL | 5.8 | 0.3 |
| IPL | 6.7 | 0.26 |

-continued

| Layer | Mean | Std |
|---|---|---|
| INL&OPL | 10 | 1.97 |
| ONL | N/A | N/A |
| PR | 143 | 4.18 |

In-Vivo Rabbit Study

Figure 2B:
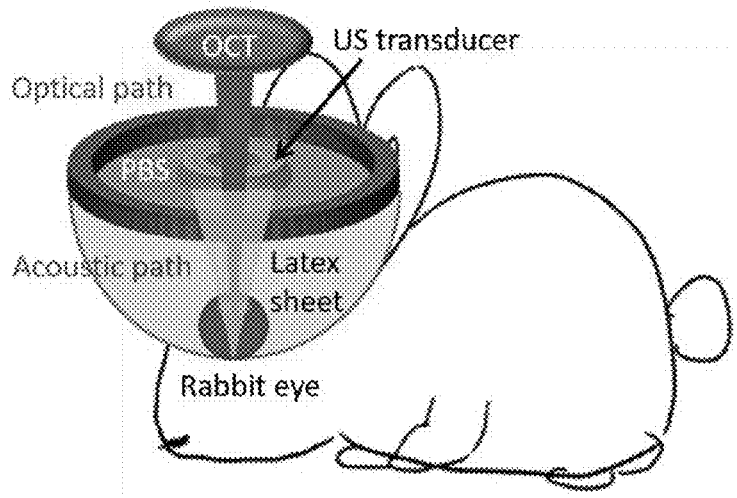
FIG. 2B shows a schematic diagram and photograph of an in-vivo rabbit experimental set up, along with a schematic of retina layered anatomy, in accordance with the present invention.
Figure 2B:
Figure 2B:
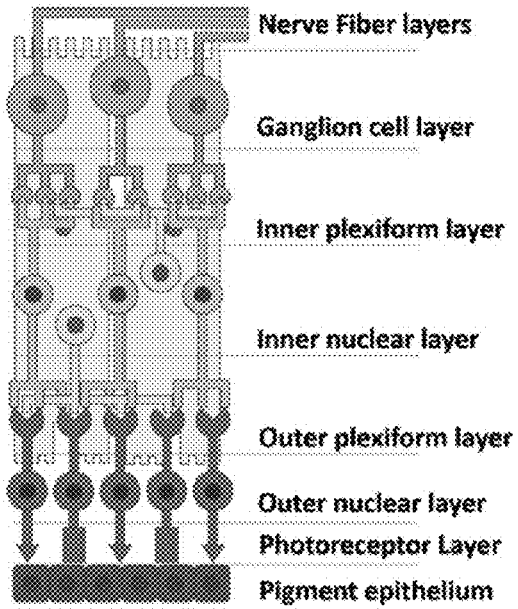

Although the elasticity contrast between different retinal layers is apparent in the ex-vivo porcine model, the presence of intraocular pressure and blood vessel perfusion is lost. Therefore, it is not an accurate representation of the retinal structure in its natural environment. In order to address these issues, an in-vivo rabbit model was designed and imaged. For the in-vivo rabbit experiment preparation, a New Zealand rabbit was used for an AMD study, where it was exposed to a high fat diet, blue light, and nicotine for 8 weeks. Since the disease was localized, most of the central retina was still relatively healthy. For this shear wave elastography study, a healthy region of the central retina was chosen. The rabbit was given 35 mg/kg of ketamine and 5 mg/kg of xylazine subcutaneously for initial anesthesia. Two drops of proparacaine HCl and atropine solution were applied topically for further anesthesia and dilation of the eye for imaging, respectively. As shown in FIG. 2B, the unconscious rabbit was propped onto the imaging stage and the eye was proptosed in the imaging setup. The rabbit eye is proptosed within a rubber drape that can serve as a container to immerse the eye in PBS fluid. The ultrasound transducer was removed in order to visualize the ocular proptosis of the rabbit. The drape system imitates the steridrapes that are used in clinical ultrasound. PBS is then added to the draped construct once again to serve as the medium for propagation as well as for lubrication of the rabbit eye. Additional anesthesia was given via subcutaneous injection of ketamine (17.5 mg/kg) if the heart rate or oxygen levels indicate distress. After imaging was completed, the rabbit was euthanized with an intravenous injection of euthasol. When death was confirmed, the rabbit eye was enucleated and fixed in 10% buffered formalin for histological analysis.

Figure 11A:
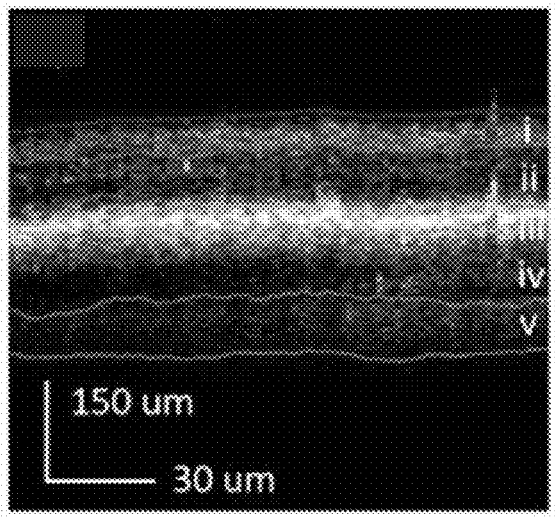
FIGS. 11A-11D show in-vivo rabbit elastography results.
Figure 11B:
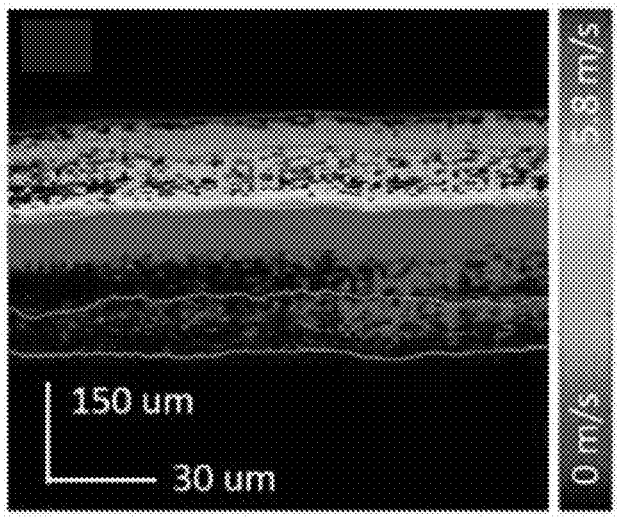
Figure 11C:
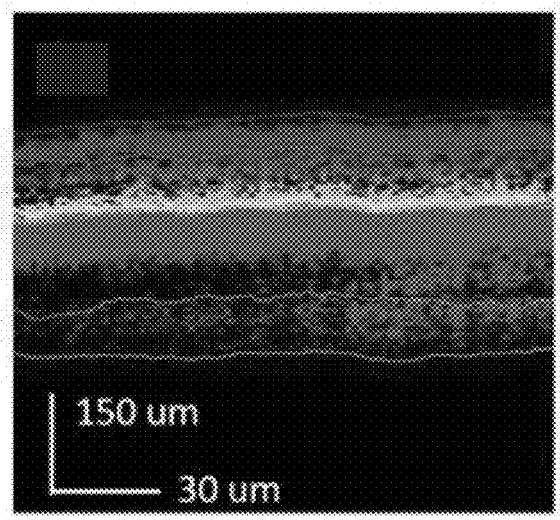

Imaging was performed on the central retina approximately 1.5 mm from the optic disc on the temporal side. The same B-M mode scanning scheme was used to capture the shear wave propagation. The OCT intensity image is shown in FIG. 11A, where segmentation was performed to isolate five different layers in the posterior globe. The shear velocity map was demonstrated in FIG. 11B and a speed of up to 5.8 m/s can be visualized. The velocity was converted to the Young's modulus in FIG. 11C. The elasticity of the first three layers from the ganglion side to the photoreceptor side are: 12.6±1.5, 35.7±18.9, 101.1±5.1 kPa. The bottom two layers of the eye could not be differentiated due to the fast propagation speed where the Young's modulus is over 100 kPa. The shear wave is attenuated within 200 um in the lateral direction and the current system setup is not fast enough to capture the wave propagation within such a distance for the bottom three layers. This issue can be resolved by increasing the imaging speed or extending the traveling distance of the shear wave with a higher ultrasound excitation power. According to the histology, the bottom two layers are close to the sclera and are expected to be stiffer than the retina and have a higher propagation velocity.

Figure 11D:
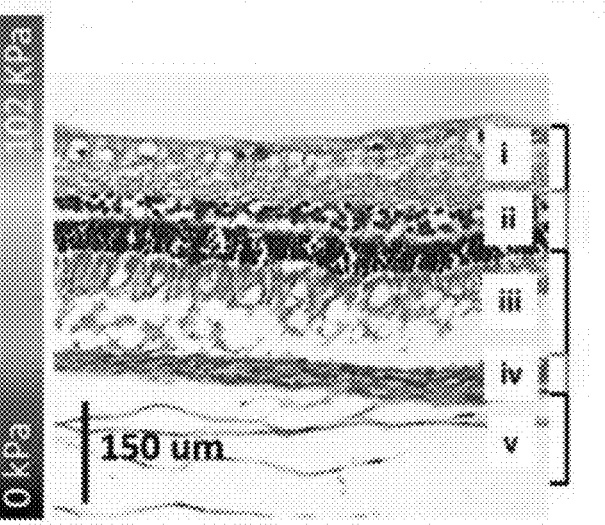

After the rabbit was euthanized, the posterior globe was fixed and processed for histological analysis. H&E staining is shown in FIG. 11D, where the layers of the retina can be corresponded to the OCT figure. Three layers of the live rabbit retina have been distinguished with different elasticity values. The feasibility of using the SW-ARF-OCE method to probe the mechanical properties of the retina has been confirmed.

In some embodiments, a higher imaging speed may be necessary to visualize stiffer posterior layers, such as the sclera. A faster line scan camera can address this issue by helping speed up the scan time and allow for spatial imaging of a single ARF pulse. The temporal resolution of shear wave propagation may be increased so that faster shear wave speeds can be tracked within stiffer tissue such as the sclera. In some embodiments, the propagation distance of the shear wave is limited to a few hundred microns due to the fast attenuation of the signal. A larger field of view can be achieved with a high power excitation pulse, more precise confocal alignment of the ultrasound excitation on retinal tissue, or the implementation of an array transducer for a larger region of excitation and detection.

In other embodiments, since a phase-Doppler was used to measure the displacement in hundreds-nanometer range and the displacement sensitivity of this imaging system is less than 1 nm, the excitation ARF can be scaled down by at least 1 order of magnitude while still obtaining sufficient signal. Moreover, with the incorporation of a faster camera, it may be possible to measure the shear wave propagation across a spatial region using a single pulse. This can decrease the patient exposure to ARF and help the translation of this technique to clinics. In further embodiments, an ophthalmic gel may be used as a substitute for the PBS bath to allow for fine tuning of the optical focus and bulk motion removal.

3-D Segmentation Based on the Combination of Dynamic Programming and Random Walker Algorithm The following is provided as a non-limiting example of 3-D segmentation. It is to be understood that other methods of segmentation may be used for the same purpose without deviating from the scope of the invention.

In 3-D dynamic programming (DP) based segmentation, the problem of edge detection is solved by searching for the shortest pathway within a graph constructed upon the images of interest. Denote $V(x,y,z)$ to be the normalized axial gradient of volumetric OCT data with the size of $X \times Y \times Z$, where X, Y, Z represent the data length in the directions of fast scan, slow scan, and depth (axial). The equations pertain to the segmentation algorithm can be shown as below.

$$C_1(x,y,z) = \min_{-d_1 \leq i \leq d_1}(C_1(x-1,y,z+i) + \alpha_1|i|+z)) \quad \text{Equation 1}$$

$$C_2(x,y,z) = \min_{-d_2 \leq i \leq d_2}(C_1(x-1,z+i) + \alpha_1|i|) \quad \text{Equation 2}$$

$$I(x,y,z) = \text{argmin}_{-d_2 \leq i \leq d_2}(C_1(x,y-1,z+i) + \alpha_1|i|) \quad \text{Equation 3}$$

$$w(i,x,y,z) = 2 - G(x,y,z) - G(x-1,y,z+i) + w_{min} \quad \text{Equation 4}$$

$$B(x,Y) = \text{argmin}_{1 \leq z \leq Z} C_2(x,Y,z) \quad \text{Equation 5}$$

$$G(x,y,z) = V(x,y,z) \quad \text{Equation 6}$$

To construct the graph, the algorithm uses $V(x,y,z)$ as nodal value $G(x,y,z)$ and measures the length between adjacent nodes using the weight function $w(i,x,y,z)$ as shown in Equation 4. In addition, the connectivity between nodes is defined so that each node is only accessible to pixels before and after it in the searching direction. Parameters $d_1$ and $d_2$ determine the number of connectable adjacent voxels during x and y directional path search respectively. Other parameters $\alpha_1$ and $\alpha_2$ are used to control the smoothness of the segmented surface.

$$w(i, x, y, z) = 2 - G^*(x, y, z) - G^*(x-1, y, z+i) + w_{min} \quad \text{Equation 8}$$

$$G^*(x, y, z) = \begin{cases} P \times V(x, y, z) & \text{if } P \times G(x, y, z) > 0 \\ A \times P \times V(x, y, z) & \text{if } P \times G(x, y, z) \leq 0 \end{cases} \quad \text{Equation 9}$$

$$P = \begin{cases} 1 & \text{when segmenting positive gradient surface} \\ -1 & \text{when segmenting negative gradient surface} \end{cases} \quad \text{Equation 10}$$

Different OCT intensity in each layer results in a different gradient polarity for each boundary, allowing for further separation between the positive and negative gradient boundary. Accordingly, the graph construction method was modified to consider gradient polarity as shown by Equations 8-10. Parameter P defines the polarity of boundary and controls the sign of node values $G^*(x,y,z)$ so that the node values on the boundary of interest are always positive. Therefore, the nodes on other boundaries with opposite polarity will add on a higher path cost to the weight function than ones on the boundary of interest, preventing the shortest path from going through them. Additionally, the negative node values can be magnified with an arbitrary constant A to further solid the barrier.

3-D DP is applied to solve for the shortest path problem, through breaking down the optimization process into iteratively small steps where the path cost to each voxel is always minimized. The algorithm starts by searching through the volumetric data in x direction, generating shortest path cost to reach each voxel as denoted by $C_1(x,y,z)$. Then, this cost function is utilized to search for the shortest path way in y direction, and the corresponding path cost to individual voxel $C_2(x,y,z)$. Equation 1 and 2 illustrate the searching process for each voxel, where the DP algorithm generates the shortest path by pairing it with the backward voxel that yields minimal accumulative cost. Additionally, the path cost is accumulated simultaneously within all the planes that are parallel to the searching direction. The axial index of the paired voxel is stored in matrix $I(x,y,z)$, so that path way can be retrieved once the terminal is established. The algorithm finishes at plane y=Y, where the terminal of the overall shortest path can be generated by finding the location of the axial minimums from the y-direction cost function $C_2(x, y=Y,z)$ as described in the Equation 5. All other boundaries can be generated by tracing back connected voxels within matrix I as shown by Equation 7:

$$B(x,y) = I(x, y+1, B(x, y+1)), 1 \leq x \leq X, 1 \leq y \leq Y-1 \quad \text{Equation 7}$$

Since the searching algorithm does not prevent the shortest path from going through several different boundaries, a rough region has to be defined before starting a search. Therefore, the algorithm was modified by defining search region adaptively based on the searching history. More specifically, the y-direction cost accumulation and boundary detection, which was previously performed in parallel within each y-z plane, is accomplished in order so that the firstly segmented boundaries can serve as reference to define the search region for the followings.

While searching for the shortest path with the adaptive method, the boundary at y-z plane x=X will be segmented first and used as reference. Because the corresponding cost function $C_2(x=X,y,z)$ is accumulated through the entire volumetric data and the shortest pathway may most likely convolve to a single boundary. Given that the inter frame distance is in the micron scale, we can assume that the layer boundary in the adjacent y-z plane x=X−1 resides in a small region that is centered by the reference boundary. Thereby the search region for this boundary and all other boundaries within a single surface can be constrained by performing this process iteratively.

Figure 6:
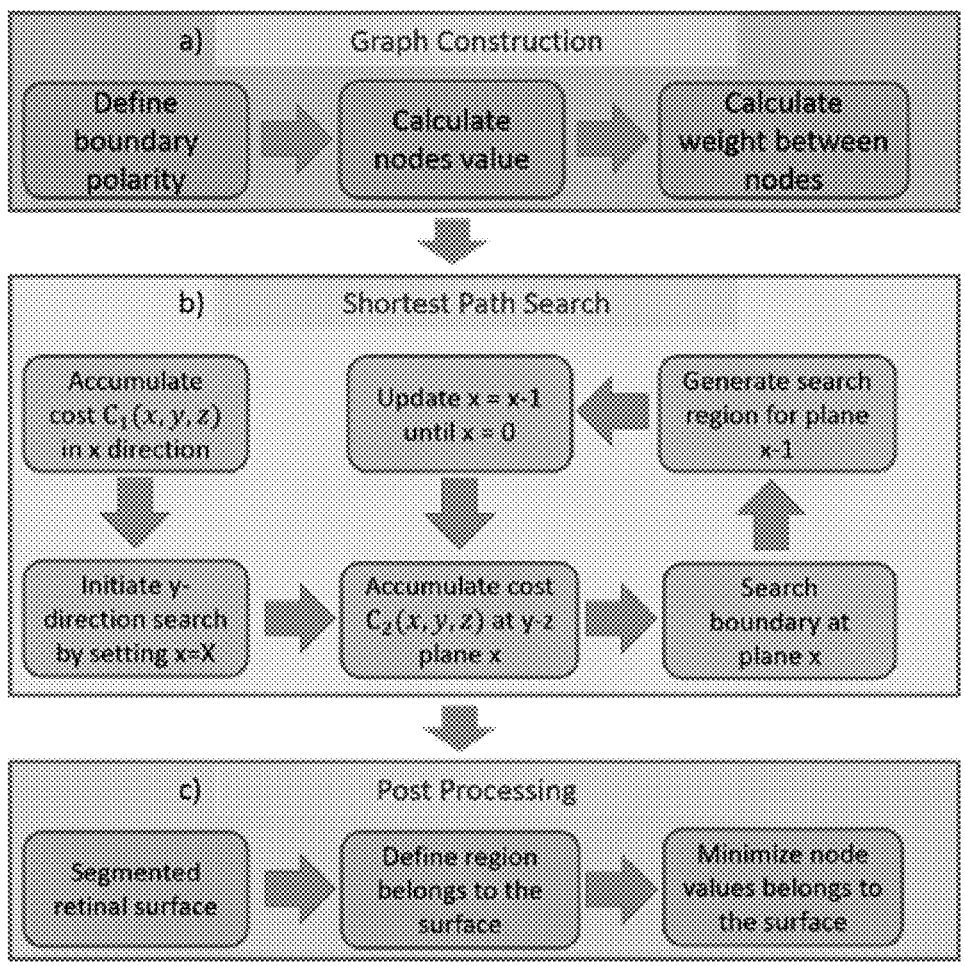
FIG. 6 is another flow diagram of 3-D dynamic programming segmentation algorithm with adaptive search region generation method.

After one surface is segmented, the gradient values of the surrounding regions must be minimized to prevent them from interfering with the segmentations of other surfaces. The axial gradient profile across a boundary tends to have a skewed Gaussian shape, with a peak at the boundary position. Thus, the profile can be split using the peak position and then fit them with two Gaussian functions to obtain the corresponding FWTM (full width tenth maximum). Finally, the gradient values are attenuated within this region by a factor of K. The width of the region is given by the FWTM of the fitted curve. In summary, the modified 3-D dynamic programming algorithm to segment one retinal layer can be illustrated by FIG. 6.

With this method, the 1st, 2nd, $4^{th}$, and 7th positive gradient surfaces can be segmented first and then the other three in between those surfaces. Since the threshold method is not used to limit the search region before segmentation, it is time extensive to calculate the accumulative functions when searching in the entire volumetric data. In order to make it practical for clinical translations, the dynamic programming method was accelerated by incorporating a Graphics Processing Unit (GPU). For instance, the code is implemented using a GPU card that yields in a segmentation speed of less than two seconds per surface over a 400×500× 600 pixel volumetric data.

Figure 7:
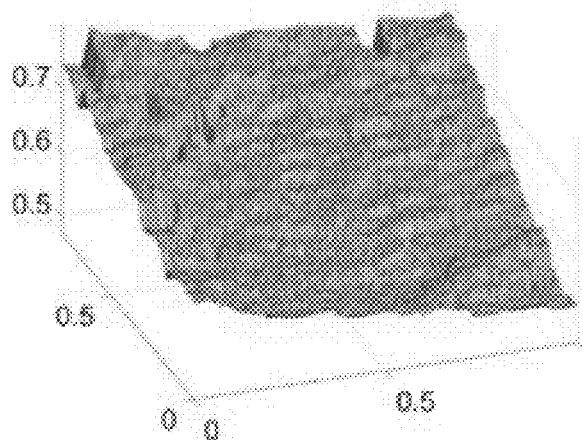
FIG. 7 shows a non-limiting example of using random walker algorithm to refine the surfaces segmented by 3-D dynamic programming.
Figure 7:
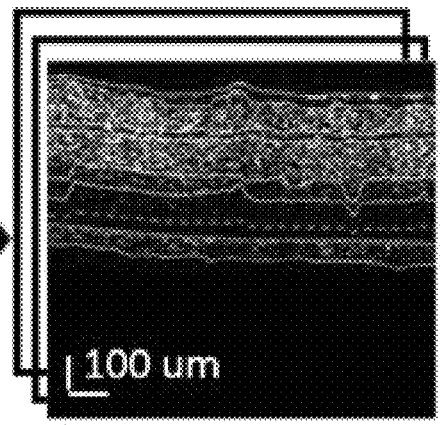
Figure 7:
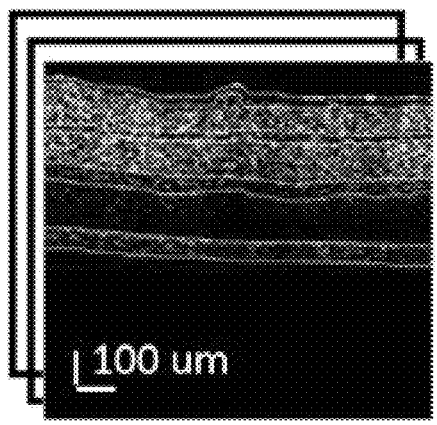
Figure 7:
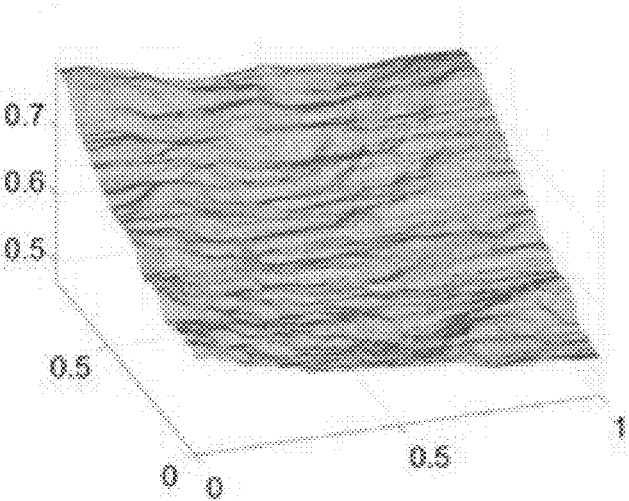

Overall, the 3-D dynamic programming gives out an accurate segmentation method for most layers of the porcine retina, with the exception of the 5th layer. It is suspected that this gradient-based segmentation method may be too sensitive to speckle noise that could overwhelm the boundary gradient of a weak scattering layer. Therefore, the intensity based random walker segmentation method is used to refine the boundaries. Random walker is a supervised segmentation method that requires prior knowledge. In the context of retinal segmentation, the segmented boundaries from the 3-D dynamic programming are used to generate seeds for the random walker segmentation. Seeds are pixels that are labeled to specific layers, which can be used by the segmentation algorithm to identify all other unlabeled pixels. FIG. 7 shows the segmentation results before and after random walker refinement, where dotted lines represent seeds.

Figure 8:
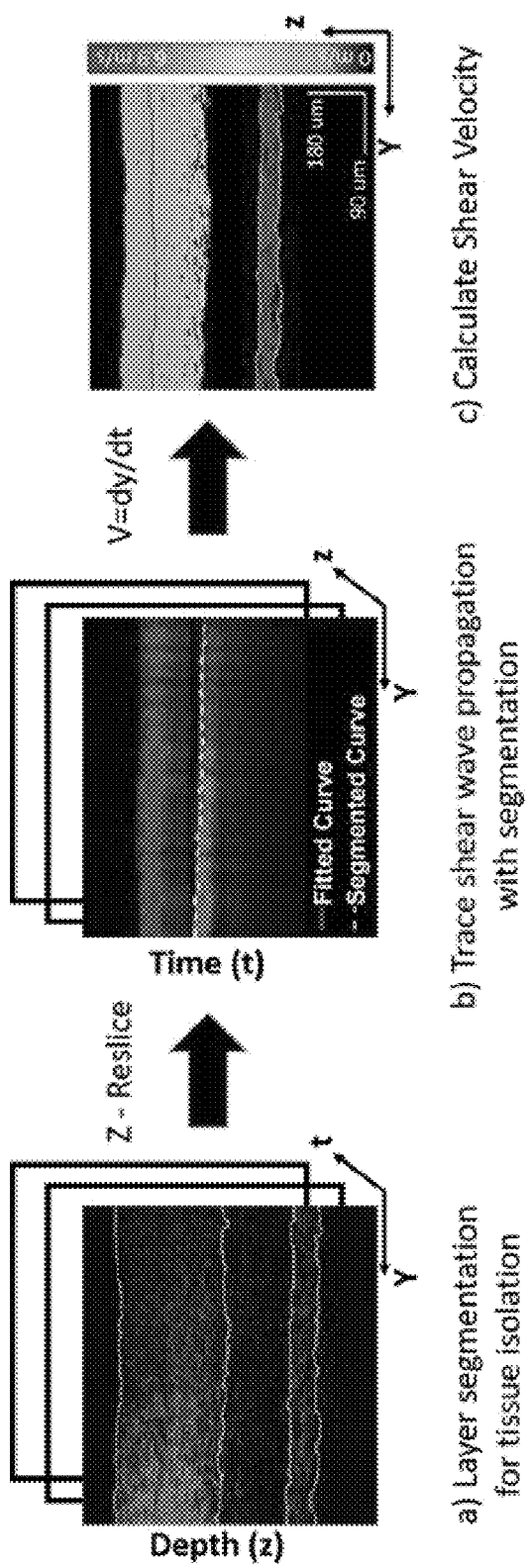
FIG. 8 is a non-limiting example of using 3-D segmentation to trace shear wave propagation by a) layer segmentation to isolate data from each retinal layer, b) segmentation to achieve the times when a shear wave reaches different positions in the y-axis, and c) calculating the spatial shear wave speed by estimating the slope of the shear wave trace identified by the segmentation in b).

FIG. 8 is a flow chart to map out the spatial shear wave speed using 3-D dynamic programming. First, the algorithm is used to identify and isolate the data of different retinal layers as shown in a). Then, the data of each layer is re-sliced along the depth direction, and images are generated showing the spatial temporal shear wave propagation as shown in b). Afterwards, the DP algorithm is utilized in segmentation of shear wave propagation and the arrival time of the shear wave to each y position is obtained. Finally, the spatial shear wave speed in c) is mapped out by estimating the slope of the segmented shear wave trace as shown in the fitted curve line of b).

In conclusion, the present invention provides a novel method to quantify the mechanical elasticity of the retinal layers in-vivo using SW-ARF-OCE based on layer segmentation and shear wave analysis. This technology offers high resolution imaging and highly sensitive velocity maps that are used to quantitatively assess retinal layers. Furthermore, the system is non-invasive and the confocal setup allows for easy access to the posterior eye. Ultrasound gel and steridrape-based waterbaths can be coupled with ultrasound into the eye. This technology will allow researchers and physicians to study the mechanisms behind changes in the mechanical elasticity of the retina during disease onset and progression, which is crucial in both basic pathological research as well as clinical diagnosis.

As used herein, the term "about" refers to plus or minus 10% of the referenced number.

Various modifications of the invention, in addition to those described herein, will be apparent to those skilled in the art from the foregoing description. Such modifications are also intended to fall within the scope of the appended claims. Each reference cited in the present application is incorporated herein by reference in its entirety.

Although there has been shown and described the preferred embodiment of the present invention, it will be readily apparent to those skilled in the art that modifications may be made thereto which do not exceed the scope of the appended claims. Therefore, the scope of the invention is only to be limited by the following claims. Reference numbers recited in the claims are exemplary and for ease of review by the patent office only, and are not limiting in any way. In some embodiments, the figures presented in this patent application are drawn to scale, including the angles, ratios of dimensions, etc. In some embodiments, the figures are representative only and the claims are not limited by the dimensions of the figures. In some embodiments, descriptions of the inventions described herein using the phrase "comprising" includes embodiments that could be described as "consisting of", and as such the written description requirement for claiming one or more embodiments of the present invention using the phrase "consisting of" is met.

The reference numbers recited in the below claims are solely for ease of examination of this patent application, and are exemplary, and are not intended in any way to limit the scope of the claims to the particular features having the corresponding reference numbers in the drawings.

What is claimed is:

1. A non-invasive system for detection of elasticity of retinal layers in a posterior of the eye, the system comprising:
   (a) a confocal shear wave acoustic radiation force optical coherence elastography (SW-ARF-OCE) system comprising:
      (i) an ultrasound transducer; and
      (ii) a confocal optical coherence tomography (OCT) system co-aligned with the ultrasound transducer, wherein the OCT system and the ultrasound transducer are configured to be disposed exterior to and on a same side of the eye;
   (b) a processor operatively coupled to the SW-ARF-OCE system; and
   (c) a memory operatively coupled to the processor, wherein the memory stores computer-readable instructions that, when executed by the processor, causes the processor to perform operations comprising:
      (i) actuating the ultrasound transducer to pulse, wherein pulsing generates a shear wave displacement at a first location of the retinal layers;
      (ii) actuating the confocal OCT system to receive OCT signals from multiple locations along retinal layers, the multiple locations being lateral to the first location, the OCT signals providing a measure of a propagation of the shear wave displacement along the multiple locations of the retinal layers;
      (iii) performing a three-dimensional (3-D) segmentation analysis on the OCT signals detected to segment the retinal layers and isolate different retinal layers for layer specified shear wave elastic analysis;
      (iv) tracing shear wave propagation with 3-D segmentation;
      (v) calculating a shear wave propagation speed at each segmented retinal layer and generate a shear velocity map at each segmented retinal layer;
      (vi) determining a shear modulus of each segmented retinal layer based on the shear velocity map;
      (vii) determining an elastic modulus of each segmented retinal layer based on the shear modulus; and
      (viii) generating an elastogram of the elastic modulus of each segmented retinal layer, thereby spatially mapping elasticity of different posterior ocular layers of the retina.

2. The system of claim 1, wherein the SW-ARF-OCE system further comprises a radiofrequency amplifier (110) operatively coupled to the ultrasonic transducer, a function generator (116) operatively coupled to the radiofrequency amplifier (110) and the processor, wherein the processor pulses the ultrasound transducer by producing a baseband signal that is converted by the function generator (116) into a sinusoidal modulated pulse signal, wherein the sinusoidal modulated pulse signal is amplified by the radiofrequency amplifier (110) and fed to the ultrasonic transducer (112), wherein the ultrasonic transducer (112) operates in a shear wave mode and generates an acoustic beam, wherein the acoustic beam is applied to the first location of the retinal layers to generate the shear wave displacement in the retinal layers.

3. The method of claim 1, wherein the OCT system comprises a light source (102), an optical isolator (104), an optical coupler (106), a reference mirror (108), a pair of galvo mirrors (114), and a line scan camera (120) operatively coupled to the processor, wherein the light source (102) emits a light that is filtered through the optical isolator (104) and then split by the optical coupler (106) into a first split light that is directed to the reference mirror (108), and a second split light that is transmitted to the pair of galvo mirrors (114), wherein a position of the galvo mirrors is adjusted such that the second split light beam is confocal with the acoustic beam in a starting location, and focal on a plurality of locations on the sample, thereby enabling detection of the shear wave displacement at the plurality of locations on the sample, wherein detection of the shear wave displacement is in a form of scattered light, which is coupled with the reflected first split light to form an interference light, wherein the interference light is separated by wavelength with a diffraction grating and focused onto the line scan camera (120), wherein a camera signal from the line scan camera (120) is further processed by the processor (122) using 3-D segmentation analysis to generate an elastogram.

4. The system of claim 1, wherein detection of a retinal disease is based on changes in the elasticity occurring at the different layers of the retina.

5. The system of claim 1, wherein the ultrasound transducer is a ring-shaped transducer or an array transducer.

6. The system of claim 1, wherein the 3-D segmentation analysis comprises segmenting boundaries of the retinal layers based on an intensity gradient across the retinal layers and further comprises refining the segmented boundaries based on absolute intensity measured at the boundaries.

7. The system of claim 1, wherein the 3-D segmentation analysis comprises one or more of a 3-D dynamic programming, a 2-D random walker algorithm, a 3-D random walker algorithm, a graph theory, machine learning, and clustering algorithm.

8. The system of claim 1, wherein calculating the shear wave propagation speed at each segmented retinal layer comprises estimating a slope of wave travel distance as a function of wave arrival time at each pixel.

9. The system of claim 1, wherein the shear modulus is determined using the shear wave speed and a tissue density, wherein the elasticity is generated based on the relationship between Young's modulus and shear modulus.

* * * * *